United States Patent
Smith et al.

(10) Patent No.: US 7,378,975 B1
(45) Date of Patent: *May 27, 2008

(54) METHOD AND APPARATUS FOR MITIGATING THE RISK OF PRESSURE SORES

(75) Inventors: Toby E. Smith, Broken Arrow, OK (US); Craig L. Cooper, Inola, OK (US)

(73) Assignee: Bed-Check Corporation, Tulsa, OK (US)

( * ) Notice: Subject to any disclaimer, the term of this patent is extended or adjusted under 35 U.S.C. 154(b) by 44 days.

This patent is subject to a terminal disclaimer.

(21) Appl. No.: 11/326,532

(22) Filed: Jan. 5, 2006

Related U.S. Application Data

(63) Continuation-in-part of application No. 10/658,622, filed on Sep. 9, 2003, now Pat. No. 7,030,764, which is a continuation-in-part of application No. 09/591,887, filed on Jun. 9, 2000, now Pat. No. 6,646,556.

(51) Int. Cl.
*G08B 23/00* (2006.01)
(52) U.S. Cl. .................. 340/573.1; 340/666; 340/667
(58) Field of Classification Search ............. 340/573.7, 340/573.1, 666, 667, 529, 309.16, 309.7; 250/227.14, 221
See application file for complete search history.

(56) References Cited

U.S. PATENT DOCUMENTS

| | | |
|---|---|---|
| 3,866,204 A | 2/1975 | Barkley |
| 4,179,692 A | 12/1979 | Vance |
| 4,295,133 A | 10/1981 | Vance |
| 4,472,847 A | 9/1984 | Gammons et al. |
| 4,484,043 A | 11/1984 | Musick et al. |
| 4,565,910 A | 1/1986 | Musick et al. |

(Continued)

FOREIGN PATENT DOCUMENTS

EP 0853918 A2 7/1999

(Continued)

OTHER PUBLICATIONS

Computerized Search by J.R. Harvey, dated Aug. 25, 1999 (2 pages).

(Continued)

*Primary Examiner*—Thomas J Mullen, Jr.
(74) *Attorney, Agent, or Firm*—Fellers, Snider, Blankenship, Bailey & Tippens, P.C.; Terry L. Watt

(57) ABSTRACT

There is provided herein a sensor/monitor combination designed to reduce the risk of pressure ulcer occurrence in immobile patients, wherein the level of patient activity is tracked to determine whether or not that patient has exhibited sufficient activity to merit eliminating a scheduled assisted relocation to a new position. The instant device senses the time since a patient last relocated into a different sitting or lying position. If the patient has not moved during some predetermined time period, the nursing staff will be notified by the invention that it is time to manually reposition the patient. If the patient has significantly changed position during the predetermined time period and, thus, allowed previously compressed tissues to reoxygenate, the invention will not signal that a move is necessary, thereby eliminating the need in some cases to rouse the patient from an otherwise healing sleep.

22 Claims, 7 Drawing Sheets

U.S. PATENT DOCUMENTS

| | | | |
|---|---|---|---|
| 4,633,237 A * | 12/1986 | Tucknott et al. | 340/666 |
| 4,653,130 A | 3/1987 | Senoue et al. | |
| 4,700,180 A | 10/1987 | Vance | |
| 4,799,276 A | 1/1989 | Kadish | |
| 4,825,486 A | 5/1989 | Kimura et al. | |
| 4,908,889 A | 3/1990 | Lonardo | |
| 5,010,608 A | 4/1991 | Barnett et al. | |
| 5,031,261 A | 7/1991 | Fenner, Sr. | |
| 5,038,137 A | 8/1991 | Lloyd | |
| 5,255,404 A | 10/1993 | Dinsmoor, III et al. | |
| 5,303,436 A | 4/1994 | Dinsmoor, III et al. | |
| 5,325,551 A | 7/1994 | Tappel et al. | |
| 5,345,634 A | 9/1994 | Sokol | |
| 5,353,012 A | 10/1994 | Barham et al. | |
| 5,511,260 A | 4/1996 | Dinsmoor, III et al. | |
| 5,526,543 A | 6/1996 | DiMatteo | |
| 5,554,835 A | 9/1996 | Newham | |
| 5,571,973 A | 11/1996 | Taylot | |
| 5,600,108 A | 2/1997 | Newham | |
| 5,611,096 A | 3/1997 | Bartlett et al. | |
| 5,623,760 A | 4/1997 | Newham | |
| 5,633,627 A | 5/1997 | Newham | |
| 5,638,558 A | 6/1997 | Moore | |
| 5,640,145 A | 6/1997 | Newham | |
| 5,652,987 A | 8/1997 | Fujita | |
| 5,654,694 A | 8/1997 | Newham | |
| 5,657,499 A | 8/1997 | Vaughn et al. | |
| 5,930,152 A | 7/1999 | Dumont et al. | |
| 5,941,836 A | 8/1999 | Friedman | |
| 5,945,914 A | 8/1999 | Holmes et al. | |
| 6,014,346 A | 1/2000 | Malone | |
| 6,030,351 A | 2/2000 | Schmidt et al. | |
| 6,065,727 A | 5/2000 | Fitzgerald et al. | |
| 6,111,509 A | 8/2000 | Holmes | |
| 6,129,686 A * | 10/2000 | Friedman | 340/573.1 |
| 6,287,253 B1 | 9/2001 | Ortega et al. | |
| 6,292,102 B1 | 9/2001 | Smith | |
| 6,307,476 B1 | 10/2001 | Smith et al. | |
| 6,320,510 B2 * | 11/2001 | Menkedick et al. | 340/573.1 |
| 6,417,777 B2 | 7/2002 | Fitzgerald et al. | |
| 6,441,742 B1 | 8/2002 | Lovely et al. | |
| 6,646,556 B1 | 11/2003 | Smith et al. | |
| 7,030,764 B2 | 4/2006 | Smith et al. | |

FOREIGN PATENT DOCUMENTS

| | | |
|---|---|---|
| GB | 2235776 A | 3/1991 |
| GB | 2329250 A | 3/1999 |
| GB | 2350681 A | 12/2000 |
| WO | WO 00/51541 | 9/2000 |

OTHER PUBLICATIONS

Computerized Search by J.R. Harvey, dated Aug. 30, 1999 (3 pages).

Computerized Search of IBM patent site dated Aug. 12, 1999 (9 pages).

* cited by examiner

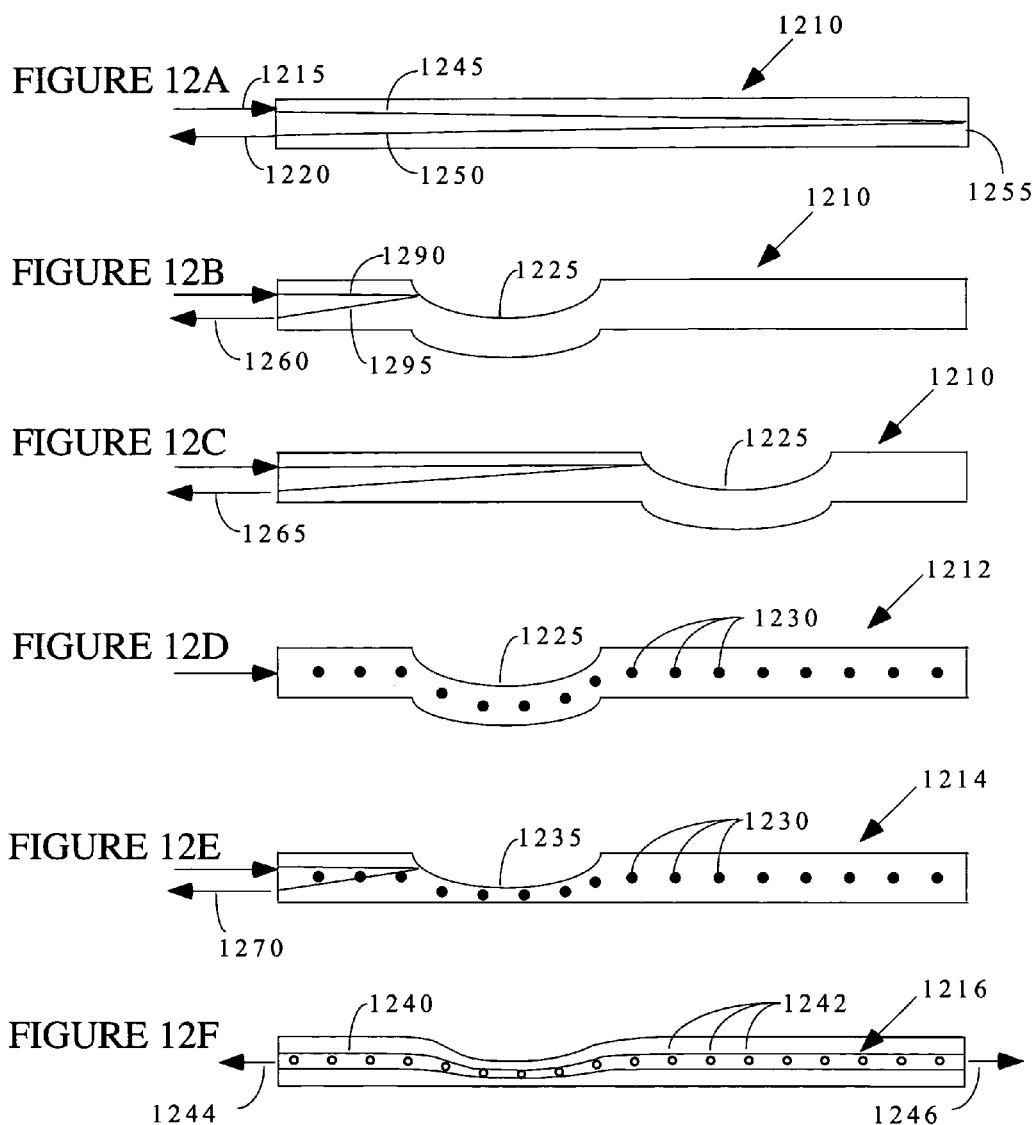

METHOD AND APPARATUS FOR MITIGATING THE RISK OF PRESSURE SORES

RELATED CASES

This application is a continuation-in-part of application Ser. No. 10/658,622 filed Sep. 9, 2003, now issued as U.S. Pat. No. 7,030,764, which is a continuation-in-part of application Ser. No. 09/591,887, filed on Jun. 9, 2000, now issued as U.S. Pat. No. 6,646,556, the disclosures of which are incorporated herein by reference as if fully set out at this point.

FIELD OF THE INVENTION

This invention relates generally to apparatus and methods for reducing the risk of immobile patients developing decubitus ulcers.

BACKGROUND OF THE INVENTION

It is well known that patients who are confined to a bed or chair for extended periods of time are at risk of developing pressure ulcers, i.e., decubitus ulcers, pressure sores, or bed sores as they are more commonly known. These ulcers are often seen to develop within soft tissue that is compressed between a bed or chair surface and a patient's weight-bearing bony prominences, the compressed tissue being at least partially deprived of oxygenated blood flow. A continued lack of blood flow, and resultant lack of oxygen, can result in cell death which may be evidenced in the form of pressure sores. Pressure sores do not become apparent immediately, but rather form over time, with the development speed depending on a number of factors including the firmness and friction of the supporting surface against the patient's skin, the tissue temperature at the site of the ischemic condition, the amount of moisture in contact with the skin, and the health and susceptibility of the skin to such injury due to age or illness.

One venerable and generally accepted means of reducing the risk of decubitus ulcer development in immobile patients is to move or turn them regularly to a position where the previously compressed tissue is no longer weight bearing, usually at approximately two-hour intervals. For example, a patient in a back rest position might be periodically rolled to one side or the other, such motion helping to maintain blood flow to soft tissue that is under compression. Similar strategies are employed for patients that are confined to a chair for long periods of time. Obviously, an assisted-movement strategy relies to a large extent on the vigilance of the (often harried) attending staff to insure that the patient is properly relocated. Further, it is far too easy for the busy caregiver to let the time for turning the patient slip by in the press of other daily emergencies. To the extent that the caregiver is too busy or forgets to perform this service in a timely manner, this method can fail to achieve its intended purpose. Further, this sort of strategy can be counterproductive for use with the patient who has some capacity for self movement as, for example, where at the next scheduled turn a patient is moved by the nurse back into a position from which he or she had just moved scant minutes before.

More particularly, the process of moving a patient to another position is admittedly disruptive to the patient and this is especially true at night, since the patient—if he or she were sleeping—will be awakened for the purpose of relocation. The typical two-hour movement interval must be observed around the clock if the method is to be effective, so it is necessary to rouse the patient—who might be sleeping soundly at the time—to make the required adjustment in position. Further, this adjustment might not have even been necessary if the patient had recently moved of his or her own volition. Thus, in many situations it would be advantageous for the caregiver to know if and when the patient last moved him or herself. Then, if the last movement were within a prescribed period of time, it might be possible to spare the patient an unnecessary interruption in his or her healing sleep. The caregiver would then relocate the sleeping patient, only if that relocation were actually required. Further, knowing which patients do not need to be moved could result in a substantial savings in labor costs, as the time that would otherwise be devoted to moving the patient that did not actually need to be moved could be productively applied elsewhere. That being said, as useful as this sort of information might be to the health care provider, however, the present state-of-the-art in patient management does not provide this sort of information.

Generally speaking, there are two broad prior art approaches to dealing with decubitus ulcers: mechanical and medicinal. The mechanical approach is aimed at reducing the severity of bedsores through the use of a specialized mattress, pad, or other arrangement, which is designed to lessen the weight-pressure that is brought to bear on the patient's bony prominences. These devices might be either static (e.g., foam, air, or water mattresses) or dynamic (e.g., compartmentally inflatable mattresses that dynamically shift the locus of support pressure under the patient in response to the patient's movements). Examples of inventions in the prior art that are generally concerned with this subject matter are U.S. Pat. No. 4,425,676, 5,926,884, and 5,072,468, the disclosures of which are incorporated herein by reference.

On the other hand, the medical—or second inventive—approach is concerned with the development of medicinal compounds and methods of treating the ulcer after it occurs. This approach is obviously useful but reactive, rather than proactive, as it attempts to minimize the damage occasioned by the ulcer after it has formed.

However, neither of the above approaches is directed toward the prevention of pressure sores which would, of course, be preferably for proper patient care.

General information relating to mats for use in patient monitoring may be found in patent application Ser. No. 09/285,956 filed Apr. 2, 1999, now U.S. Pat. No. 6,307,476, the disclosure of which is specifically incorporated herein by reference. Additionally, U.S. Pat. Nos. 4,179,692, 4,295,133, 4,700,180, 5,600,108, 5,633,627, 5,640,145, and 5,654,694 (concerning electronic monitors generally) contain further information generally pertinent to this same subject matter, as do U.S. Pat. Nos. 4,484,043, 4,565,910, 5,554,835, and 5,623,760 (switch patents), and U.S. Pat. No. 6,646,556 and patent application No. 60/487,021 (mats for use in preventing decubitus ulcers) the disclosures of all of which are all incorporated herein by reference.

Heretofore in the patient monitoring arts there has been no apparatus or method aimed specifically at reducing the risk of bedsores in a semi-invalid patient, i.e., the patient who at least occasionally moves without assistance. With a semi-invalid patient, assisted repositioning—whether manual or mechanical—should only take place if the patient has not moved for some particular period of time. This, of course, suggests the need for a method and apparatus for monitoring the patient so that the time when he or she last moved can be determined. Further, the duration of the patient's move should also be monitored to ensure that tissue reoxygenation takes place. Finally, there is a need for an apparatus that can monitor, record, and report the overall amount of patient self-induced and/or caregiver assisted movement, so as to give the caregiver (or that person's supervisor) some estimate of the amount of movement by the patient in the bed with respect to time. Those of ordinary skill in the art will recognize that historical estimates of the overall amount of patient movement are directly useful to the staff and further useful in generating, for example, decubitus ulcer patient risk indices such as the Braden or Norton scale.

Heretofore, as is well known in the patient monitor arts, there has been a need for an invention to address and solve the above-described problems. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a sensor for use in patient monitoring situations, wherein the patient's motion within the bed or chair is tracked over a given period of time for purposes of determining whether or not that patient has exhibited body area contact change over time to merit eliminating a scheduled assisted relocation to a new position. According to one preferred embodiment, the instant device operates to sense the length of time since a patient has last moved from a previous sitting or lying position. If the patient has not moved during, for example, the prior two-hour period, it is preferred that the nursing staff be notified that it is time to manually reposition the patient. On the other hand, if the patient has changed position within the specified window, the device will note that fact and withhold its reminder to the nurse or other caregiver that the patient needs to be moved at the next scheduled relocation time, thereby eliminating the need in some cases to rouse the patient from an otherwise healing sleep. In either case, the instant invention operates to mitigate the risk that a patient will develop bed sores by helping ensure that the patient is manually moved as frequently as is medically necessary, but no more often than is actually necessary, based on patient movement history.

In accordance with another aspect of the instant invention, there is provided an electronic monitor for use with a patient sensor which is designed to monitor the patient's position and calculate his or her degree of activity in the chair or bed. In the preferred embodiment, the monitor consists of a microprocessor in communication with a patient sensor (discussed below). The microprocessor will be equipped to ascertain—by reference to the attached sensor—an initial position of the patient within the bed. Once an initial position is determined, the monitor will then continue to watch the patient's position, looking for significant changes in that position, wherein a significant change in position is one wherein the patient moves from a current position within the bed and maintains that move (i.e., does not return to the original position) for a period of time that is sufficient to reoxygenate the previously compressed tissue to some safe level. If such a change has not occurred before the passage of some predetermined time interval, the monitor will enter into an "alarm" or signaling state. Depending on the settings selected by the operator, the monitor might: cease generation of a white noise signal, emit an audible alarm, signal a nurses' station, initiate a visual alarm (e.g., a flashing light), etc., that would serve warning to the caregiver that it is time to turn the patient. Needless to say, although the preferred embodiment of the instant invention calls for a device that gives notice to the care giver when the patient needs to be repositioned to a different body contact area, the invention disclosed herein could as easily be modified to notify the caregiver when the patient does not need to be moved.

On the other hand, if the patient demonstrates a significant change in position prior to the expiration of the predetermined turn interval the microprocessor in the electronic monitor will note that fact and reset the timer, preferably to its initially specified time interval. This change in position may or may not be accompanied by the sending of a signal to the care-giving staff to inform them of that fact. The microprocessor will then continue to monitor the patient's position via the sensor until either the current time period expires or the patient moves significantly again.

Broadly speaking, the hardware of the instant invention consists of two functional components: a position sensor and an electronic monitor. In the preferred embodiment, the electronic monitor and sensor will be separate devices. However, it is certainly possible, and well within the skill of one of ordinary skill in the art, to combine these two functions into a single operating unit. That being said, preferably, and as described below, two separate modules will be utilized. In broadest terms, the position sensor component generates signals in response to the location or orientation of the patient in the bed or chair. The electronic patient monitor senses and interprets the signals from the position sensor and, in the preferred embodiment, handles the timing, arming and disarming of the associated alarms and communications with the nurses' station.

The sensor portion of the instant invention, which might be any one of a number of different devices, must at minimum be capable of sensing a change in the patient's position, location, or orientation within a bed or chair. Examples of devices that might be suitable for use with this invention include a pressure sensitive bed or chair mat, a temperature sensitive bed or chair mat, pressure sensitive mats placed underneath the feet of the hospital bed, capacitive mats, inductive mats, accelerometers in communication with the springs of the bed, infrared motion detectors, optically activated mats (as is discussed below), strain gages, inclinometers (as is discussed below), sensors detecting localized deflection of the bed or mattress, etc.

A minimal requirement of the electronic monitor is that it be able to sense patient position information as provided by the sensor. Additionally, it must be able to track the passage of time in at least some rudimentary fashion, so as to determine the time interval between patient movements. In the preferred embodiment, the monitor will include a microprocessor or microprocessor-like device (including assemblies of discrete logic or analog components) which can implement the logic described below and, additionally, can function as a clock if need be. Finally, in the preferred embodiment the monitor will be able to use the sensor information to differentiate between body movements that are only slight shifts in position and other movements that actually result in a change the patient's weight supporting points that is maintained long enough to at least partially reoxygenate the previously compressed tissues.

Turning now to various embodiments of the instant monitor, according to a preferred embodiment of the instant invention, there is provided a monitoring device substantially as described previously, but wherein a patient movement threshold is established such that only significant movements are sufficient to cause the device to reset withhold notification of the nursing staff to turn the patient, thereby letting the patient continue to rest.

As is described in more detail hereinafter, a significant movement is one wherein the patient moves to a new location and then that new position is maintained for a predetermined period of time, wherein the designated predetermined time period is sufficient to allow for reoxygenation of the patient's weight bearing tissues. That is, if a patient moves, but then returns to nearly the original position within a short period of time (e.g., within ten minutes), the monitor timer will not be reset, and at the appropriate time the staff will be called to turn this patient according to the originally established preset timed schedule.

According to another aspect of the instant invention, there is provided a patient monitor substantially similar to that described above, but wherein the accumulated timed movement of the patient is monitored. Thus, if the patient is sufficiently restless but no single movement event amounts to a significant relocation, that patient might still not need to be turned because, for example, they may not have accumulated enough time in any one position to cause a problem. A preferred embodiment of the instant invention will detect and respond to that sort of condition.

According to still another aspect of the instant invention, there is provided a patient monitor substantially similar to that described above, but wherein the time interval between patient turnings (i.e., "turning time", hereinafter) is not a fixed interval but is adjustable according to parameters specified by a caregiver. For example, it is possible that the turn interval might be based on some staff estimate of the patient's tissue reoxygenation time for a particular part of the body in view of patient-specific variables such as vascularity, prior scaring, diabetic conditions, patient weight, the nature of the support surface, anemia, general health, sleeping patterns, agitation/emotional state, Braden or Norton scale scores, etc. Many other variations are possible and have been contemplated by the instant inventors.

In the preferred embodiment the sensing device will be a pressure-sensitive bed mat which is placed underneath a weight-bearing point of the patient. The mat will preferably be designed to sense at least one point of contact along its length, i.e., it will be able to determine the distance from one of its ends to the nearest point where the patient's weight compresses the mat. Obviously, for a completely motionless patient, this parameter (distance-to-contact-point) will be unchanging. However, if the patient rouses and moves, the point of contact will change—at least during the time that the patient is moving. It may be that the patient will completely remove his or her weight from the mat before settling back down again. If the patient is out of bed for more than a brief time that would typically be sufficient reason to reset the movement timer. Additionally, a "bed exit" alarm could be sounded to alert the caregiver that the patient is no longer in the bed, if that function has been selected by the user. However, the more likely scenario is that the patient will simply roll from one side to the other without ever completely removing weight from the mat. In that case, the monitor will note the change in patient position—as measured by the change in distance to nearest contact point—and, depending on its parameter settings, determine whether that movement is significant and, thus, merits resetting the turn interval timer. Finally, it should be noted that one advantage of using a mat-type arrangement as described here is that the sensor could then double as an exit mat, if that is desired. Of course, whether the mat is positioned in, on, or under the mattress is a design choice that is well within the abilities of one of ordinary skill in the art.

According to a further embodiment, there is provided an electronic monitor as described above, but wherein the electronic monitor begins to sound a local warning a predetermined period of time before it is scheduled to signal the caregiver. That is, in the preferred variation of this embodiment the electronic monitor might begin to make a relatively unobtrusive noise such as a chirp or beep (say) five minutes before the nurses' station was due to be notified. This noise might be enough to rouse the patient so as to cause him or her to turn without assistance. In other variations, the monitor, instead of broadcasting some sort of noise in an effort to rouse the patient, might cease its broadcast of soothing sounds (e.g., white noise or music) some length of time minutes before the turn alarm activates (e.g., 10 minutes before), to see if such a cessation would rouse the patient. Of course, combinations of these two approaches (ceasing the broadcast of soothing sounds and beginning to broadcast more intrusive sounds) could certainly also be utilized to greater advantage. On the other hand, if the patient does not move by the predetermined time the nurses' station will be signaled. The instant embodiment has the advantage of helping patients to learn to turn themselves, while increasing the quality of their sleep by reducing the number of times the staff must wake and move them.

The foregoing has outlined in broad terms the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to cover all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which:

FIG. 12 contains a schematic illustration of a preferred sensor which utilizes an optical source to determine patient position.

DETAILED DESCRIPTION OF THE INVENTION

According to a preferred aspect of the instant invention, there is provided a monitor and sensor, wherein the sensor is configurable to sense a position of a patient in a bed, chair, etc., and be responsive to changes therein. The electronic monitor, which is preferably kept in regular communication with the sensor, tracks the status of the sensor and responds according to its pre-programmed instructions when a patient moves or when a patient does not move for some period of time.

PREFERRED ELECTRONIC MONITOR EMBODIMENTS

Figure 1:
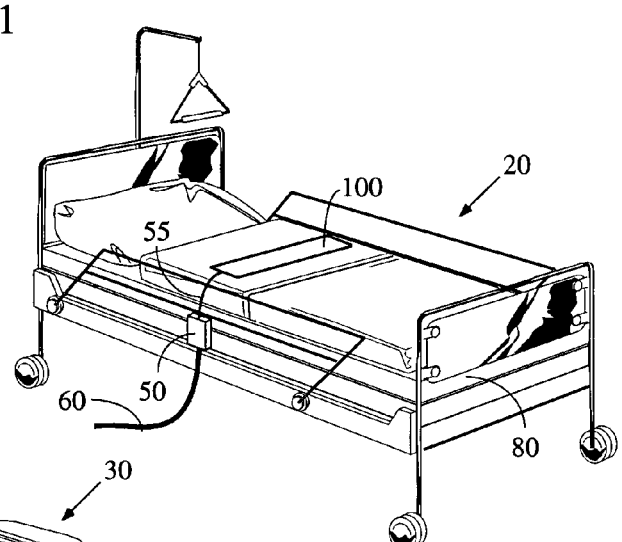
FIG. 1 illustrates a preferred embodiment of the instant invention as it would be used on a bed.

As is illustrated in FIG. 1, in the preferred embodiment the instant invention utilizes both an electronic patient monitor 50 and a sensor 100 which is typically interconnected to the monitor 50 by electrical line 55. The function of the electronic monitor is to track changes in patient position (as measured via the sensor) and act on those changes according to its pre-programmed instructions (e.g., FIG. 4). Note that the monitor might be battery powered or supplied with external power. Either configuration would be suitable for use with the instant invention. Note that patient monitor 50 and sensor 100 could readily be combined into a single unit, but FIG. 1 has not been drawn that way for purposes of clarity. Further, it should be clear that the sensor 100 could be inside of, on top of, or underneath the mattress according to the design goals of one of ordinary skill in the art and is shown on top of the mattress only for purposes of clarity.

Figure 3:
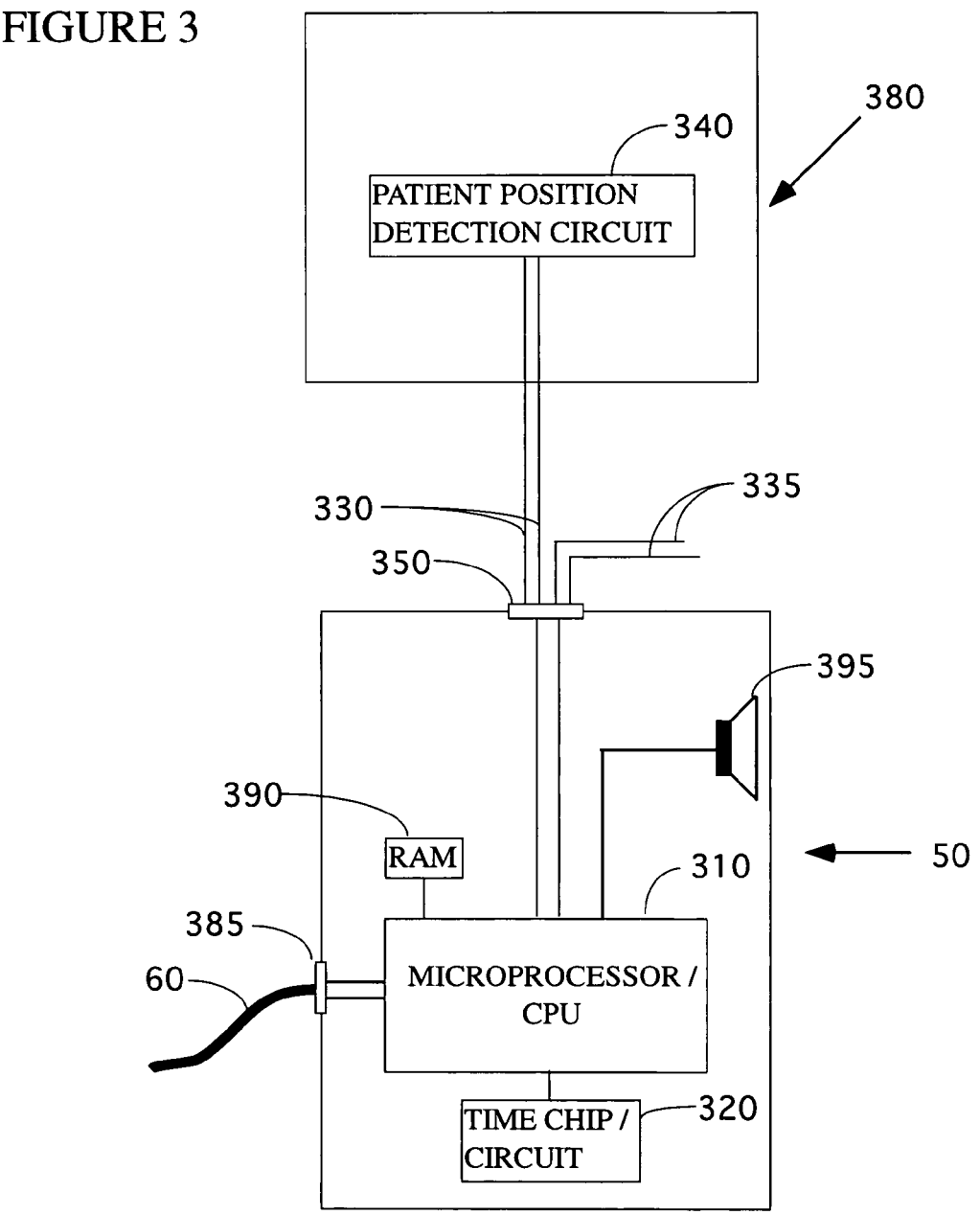
FIG. 3 contains a schematic drawing of a preferred monitor/sensor arrangement.

FIG. 3 contains a functional illustration of a preferred monitor 50/sensor 380 arrangement. In the preferred embodiment, the monitor 50 will contain at least one microprocessor/CPU 310 for the execution of pre-programmed instructions. The CPU 310 is in electronic communication with the patient detection/position circuit 340, preferably through connector 350. In the preferred embodiment, the interconnecting wire will contain at least four electrically isolated leads: 330 and 335. Although only two such electrical lines 330 are strictly necessary to sense the patient's position, it is conventional to use a three- or four-element wire. The other electrical lines 335 are available for other purposes.

Connector 385 is provided to allow the microprocessor 310 to send a signal to a remote receiver such as a nurses' station, if that is needed. In the preferred embodiment, a connecting wire 60 will connect the monitor 50 to the nurse call network, which is conventionally accessed by way of a ¼" phono-type plug. Of course, it is envisioned that an alarm might be sounded locally (e.g., from an audio speaker 395 that is preferably built into the monitor) in addition to (or instead of) notifying the nurses' station. When the monitor 50 is placed on a wheel chair, a local alarm may be the most practical solution. For purposes of the instant disclosure, the term "alarm" will be used in its broadest sense to refer to any method of notifying a caregiver of a change in the patient status via a local or remote speaker, flashing light, pulsating signal (e.g., of the sort used in conventional pagers), change on the screen of a computer monitor, or similar signaling mechanisms which are responsive to commands from the CPU 310 and which can be used to obtain the attention of a caregiver. Of course, a "speaker" 395 includes without limitation devices such as piezoelectric devices, magnetostrictive devices, electrostatic and electromechanical (e.g., buzzers) devices, or any audio annunciator/device. Thus, when the term "speaker" is used hereinafter, that term should be construed in the broadest possible sense to include any device capable of emitting an audible alarm signal under the control of the microprocessor 310. Additionally, when speaker is used herein that term should also be taken to include an associated power amplifier to drive it, if one is necessary (as it often will be). Finally, it should also be noted that it is not an essential element of the instant invention that the speaker 395 be found within the body of the monitor. The speaker 395 could also be mounted externally thereto, and, as an extreme example, might by located in an adjacent hallway or at the nurses' station.

Additionally, the connection 60 might be used to place the CPU 310 in electronic communication with any number of other remote devices, including, but not limited to, remote networks, computers, etc. Alternatively, it is known in the art to provide the electronic monitor 50 with additional communications hardware including, for example, a serial port, a parallel port, a USB port, a fire wire port, an infrared communications port, Bluetooth, Wifi, etc., all of which would preferably be accessible by the microprocessor 310.

Figure 4:
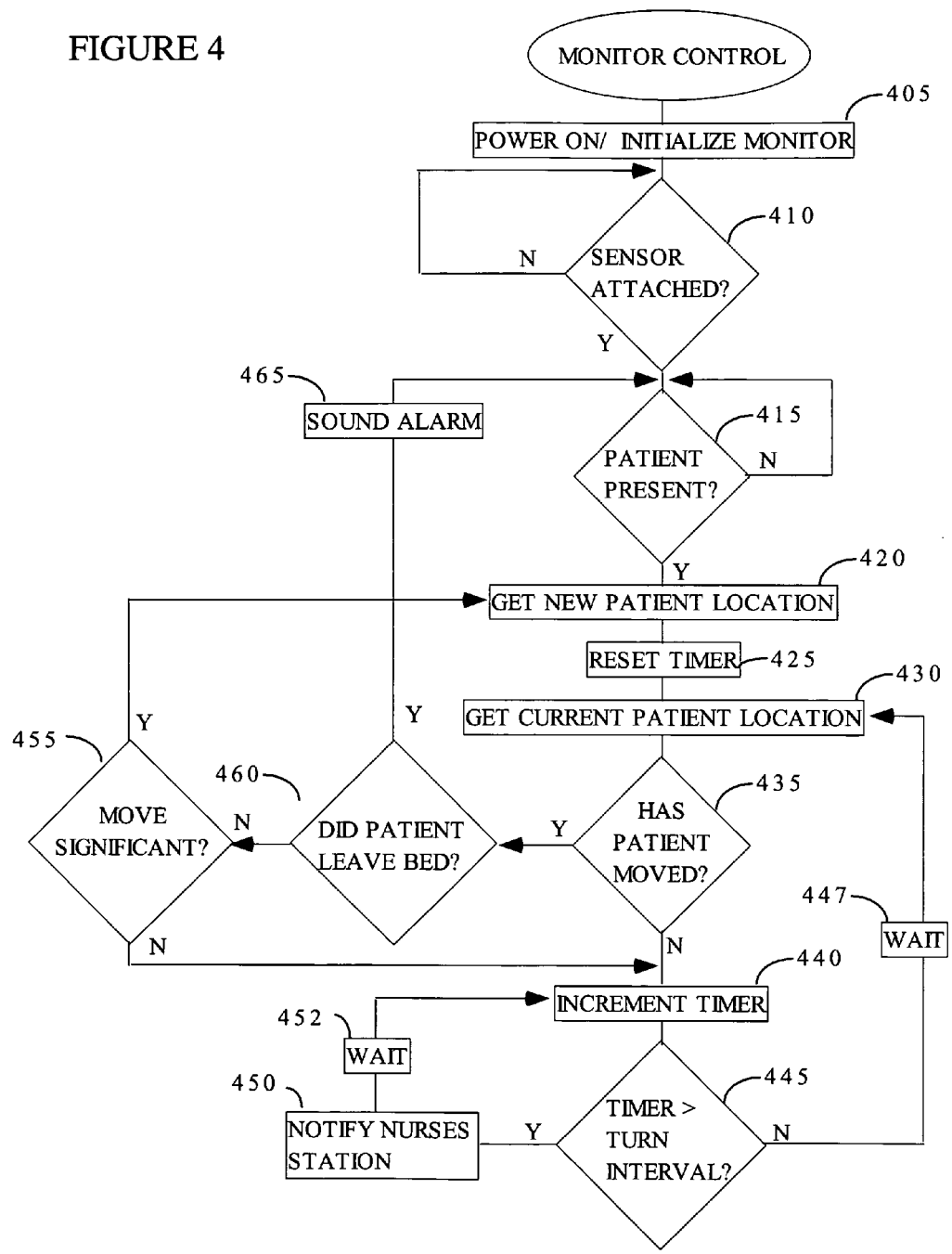
FIG. 4 is a flow chart that illustrates a preferred logic for use with the electronic patient monitor.

FIG. 4 contains a preferred logic for use by the CPU 310. As is indicated in that figure, at power-up the CPU 310 will typically initialize various internal variables (step 405), perform internal quality control checks, determine whether or not a sensing device is attached (step 410), etc. These sorts of steps are preferably done in preparation for normal operation. As a next preferred step, the CPU 310 will attempt to determine whether or not a patient is present in the bed, chair, etc. This might be done many ways, but in the case where the sensor is a pressure sensitive bed mat 100 or chair mat 200 this step 415 is easily accomplished by checking to see if the patient's weight has "closed" the sensing switch.

Of course, exactly how the monitor 50 might make this determination 415 will depend on the sort of sensor that is used.

As a next preferred step, the CPU 310 will query the sensor to determine the patient's initial position (step 420). Again, exactly how this is determined will depend on the sensor that is used: some specific examples will be discussed below. The initial position will be stored—preferably in the monitor's RAM 390—for later use. Additionally, the time at which the initial position was determined will preferably also be stored or, equivalently, a timer will preferably be zeroed to indicate the start of a measurement interval. Of course, the term RAM should be interpreted in its broadest sense to include any sort of volatile or nonvolatile storage that can be accessed by a microprocessor.

Preferably, a timer will be reset (step 425) to zero, signifying the start of a new time measurement period. As is conventional in these sorts of timing situations, the timer will preferably be incremented at intervals 425 corresponding to the frequency at which the CPU 310 checks the patient's status. Obviously many alternative arrangements are possible, including direct time interval calculations from successive calls to a time chip/circuit 320, e.g., by "subtracting" an earlier clock time from a later clock time. Additionally, it should be noted that it is not necessary to equip the instant monitor 50 with a true "time chip" as that term is understood to those skilled in the art but, instead, the CPU 310 can be instructed to "count time" by repeatedly performing an operation whose time duration is at least approximately known (e.g., incrementing the value of an integer variable or executing a timing loop). Thus, in the text that follows any reference to a "time circuit" or "time chip" should be construed as broadly as possible to include discrete hardware for determining the current time or the passage of same, as well as timing loops that are performed within the CPU 310. Those skilled in the art will recognize that there are a multitude of ways to accomplish the general goal of determining a time since a patient last moved including, of course, a real-time clock.

As a next preferred step, the CPU 310 determines the then-current position of the patient (step 430). By comparing the most recently determined position 430 with the initial position 420 established previously, it will be possible to determine whether or not the patient has moved since the earlier reading was taken (step 435). Of course, the preferable way of making this determination is to compare (e.g., subtract or difference) the numerical value(s) corresponding to the current patient position with the numerical value(s) corresponding to the initial patient position. A non-zero difference indicates that the patient has adjusted his or position or moved. More generally, there are many ways of producing a differential movement measure that do not require subtraction, although that is the preferred embodiment. For example, taking ratios of the two location values would also have some utility. Even more generally, comparisons could be based on the actual signals received from the location sensor 100 rather than converting those signals into actual distances or locations. Thus, if the sensor 100 determines patient location from, say, the measurement of capacitance, mathematical or logical operations might be performed directly on the sensed capacitance values themselves to produce a differential movement measure which is correlated with patient movement.

Note that the exact method by which the patient's position is determined is dependent on the choice of patient sensor. However, for purposes of the instant monitor embodiment, it will be assumed that the patient's position is available as a measure of the distance from the edge of a bed mat to the nearest point where the patient's body weight compresses the two halves of a pressure sensitive mat into contact. Additionally, it is preferred that the amount of the mat that is occluded by the patient's weight also be determined, as that will give some estimate as to the patient's orientation within the bed (e.g., at rest on his or her back, on a side, etc.).

If the patient has not moved since the initial determination of his or her position, the timer is preferably incremented 440 and compared with the pre-determined turn interval (step 445), the amount of increment preferably being related to the amount of time that has transpired since the last time the patient's location was checked.

As a next preferred step, the elapsed time is compared with the predetermined turn interval (step 445) as specified by the physician or other caregiver. If the elapsed time is less than the predetermined turn interval, the CPU 310 then preferably waits (step 447) before checking the current patient location again 430. Of course, the amount of time that the CPU 310 delays before obtaining the next patient location 430 might be any amount of time from zero to several minutes, with the preferred amount of delay 447 being, by way of example, several seconds.

In the event that the elapsed time exceeds the preset turning time interval and the patient has not moved, in the preferred embodiment the nurses' station 450 will be notified. Alternatively, an alarm might be sounded from a speaker 395 built into the monitor 50, a light might be flashed on the unit 50, a light might be flashed in the hall outside of the room, or any number of other actions (e.g., a remote nurse call alarm might be sounded, a pager might be activated, etc.) might be taken to notify the care giver that it is time to turn this particular patient. Any number of alternative means might be used to signal the caregiver and those skilled in the art are well able to devise many such signaling arrangements.

In the event that the elapsed time exceeds the preset turning time interval, in the preferred embodiment the nurse's station 450 will be notified via a nurse-call or a similar (e.g., wireless) communications method. Alternatively, an alarm might be sounded from a speaker 395 built into the monitor 50, a light might be flashed on the unit 50, a light might be flashed in the hall outside of the room, or any number of other steps might be taken to notify the caregiver that it is time to turn this particular patient. Any number of alternative means might be used to signal the caregiver and those skilled in the art are well able to devise such alternative signaling arrangements.

Additionally, and as a further preferred embodiment, it is preferable that the timer continue to accumulate time until the patient is actually moved by the staff (steps 452, 440, 445, and 450). By continuing to monitor the patient's condition while the patient is awaiting turning—and noting the elapsed time since the nurses' station was notified—, some measure can be obtained of the responsiveness of the staff to the patient's needs. As before, the length of time that the CPU 310 waits (step 452) may be preselected by the programmer and/or specified by the caregiver. Additionally, it is anticipated that it might be necessary in some instances to send more than one notice to the nurse's station 450 depending on the length of time that it takes for the staff to respond, and steps 452, 440, 445, and 450 allow for and implement that as a possibility. Also, note that communications to the nurses' station might be made "progressive" in urgency by continuing to alarm at higher levels of responsibility as the proceeding alarm remains unanswered.

Turning now to the case where the patient has changed position, in the preferred embodiment a further step 455 is taken to determine whether the move was significant. If the move was not significant, the timer is not reset and continues to accumulate time 440 (i.e., was the move to a new location maintained long enough to reoxygenate the at risk tissue). The purpose of this step is to prevent the timer from resetting in those instances where the patient has only shifted position momentarily, e.g., if they briefly rolled to one side but then immediately returned to their original position. In that case, it is not advisable to reset the timer, because the region of the patient's body that was at risk before the move is still at similar risk. Obviously, the time interval during which the patient has persisted in the movement from the original position, as well as the nature of the movement (e.g., front to side, front to back, sideways scoot, etc.), could be used to help determine whether a move was significant. Preferably, a movement will be flagged as significant only if it persists for, say, more than ten minutes, i.e., the patient maintains the new position for at least ten minutes before returning to his or her original position, thereby allowing time as selected by the caregiver for reoxygenation to occur. Of course, and as was discussed previously, in the context of the instant invention reoxygenation should be understood to mean reoxygenation to a point where the risk of tissue damage has been greatly reduced or alleviated.

Finally, it may be the case that the patient is restless and has performed a number of small relocations, none of which individually might amount to a significant move. However, in some cases when these moves are considered in concert, they could obviate the need to turn the patient or to extend the turn timer by some relative amount based on cumulative reoxygenation time. In that case, the cumulative amount of motion of the patient might be calculated over some time period to see if a suitable composite activity level has been achieved, the analysis potentially combining the clock-time that each (non-significant) movement took place, the change in patient orientation during the moves, the amount of time the patient remained in each position, etc. Obviously, the movement history of the patient might be accumulated locally in RAM 390 or stored remotely, if the appropriate computer networking connections are available. Such a historical record might have value for purposes of patient diagnosis, caregiver quality control, government regulations, etc. The significant movement trigger could further be customized, preferably by the caregiver, to reflect the sort of illness or injury that the patient is being treated for. Obviously, many variations on this basic idea are possible and have been specifically contemplated by the instant inventors.

However, in the event that the patient sensor indicates that the patient has moved, a next preferred step 460 is to check to see if the patient has left the bed. In the event that the sensor is a bed mat (e.g., 100) it would be a simple matter to use the CPU 320 to determine whether the circuit was "open" (e.g., a pressure sensitive mat was not "compressed" by the patient's weight), and, thus, the patient had apparently left the bed. Indeed, this is the preferred embodiment of the instant invention: a bed mat 100 that can also be used to sense a patient's position thereon. With other sorts of sensors, other methods of determining whether the patient has left the bed are available. Some of the preferred ways will be discussed below. Of course, it is preferred that the check for a bed exit be made immediately after a patient movement is sensed, thereby reducing the chances that the patient will be able to leave the bed before a caregiver arrives.

If the patient has not left the bed, the preferred next step is to obtain a new patient location 420 and save that value for comparison against future movements. Additionally, it would be appropriate to reset the timer (step 425) before entering the patient checking loop (i.e., steps 435, 440, 445, 447, and 430).

However, if the patient has left the bed 460, preferably the patient monitor will notify the caregiver of that fact through the use of an identifiable signal that is sent to the nurses' station (step 465). In the event that it has been deemed inadvisable to allow the patient o leave the bed for health reasons, this signal will alert the nurses that they should investigate the status of this patient. Alternatively, the electronic monitor 50, if it is equipped with a speaker as many such monitors are, might sound a local alarm. Obviously, many variations of this basic arrangement are possible and have been contemplated by the instant inventors.

Turning to another aspect of the instant invention, there is provided an electronic monitor substantially as described above, but wherein a pre-alarm signal is initiated locally at the monitor 50 beginning some predetermined period of time before the turn interval expires. More particularly, it is anticipated that in some instances it might be desirable to have the monitor 50 begin to sound some sort of "alarm" before the expiration of the turn interval to encourage the patient to move on his or her own. The patient, if he or she is in a condition to hear and respond to the sound, will be thereby encouraged to move to a new position so that it will not be necessary for the staff to manually relocate him or her. In the preferred embodiment, the sound that is generated will be a relatively unobtrusive noise such as a "chirp" or low "beep", a sound that would be sufficient to notify an "alert" patient but that would not unduly disturb a resting patient and that would not disturb patients in adjoining beds or rooms. Preferably, the alarm will come from a speaker 395 which has been made a part of the monitor 50. Of course, many alternative arrangements are possible, including having the pre-turn alert come from a remote speaker. This alert could also take the form of a flashing light or other standard signaling mechanisms, however preferably sound will be used. Optionally, the volume of the alarm could be increased as the time to call the nurse draws closer.

PREFERRED SWITCH EMBODIMENTS

Mat Embodiments

Figure 7:
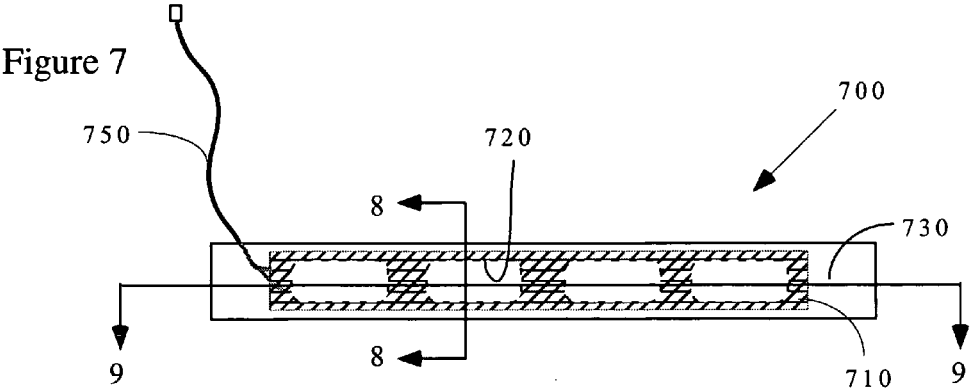
FIG. 7 illustrates the major components of a pressure sensitive mat.
Figure 8:
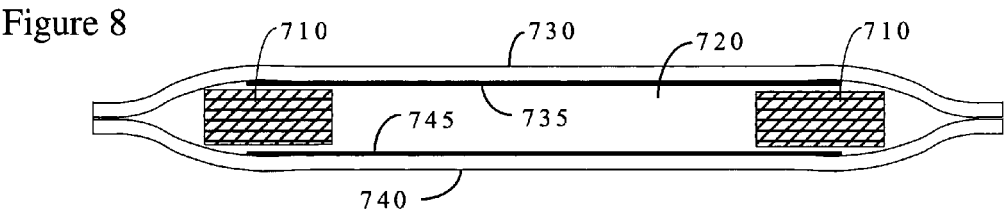
FIG. 8 contains an illustration of a transverse cross section of the mat of FIG. 7.

Turning first to FIG. 1 wherein the general environment of the instant invention is illustrated, in a preferred arrangement a pressure-sensitive sensor 100 is placed on a hospital bed 20 in an area of the bed that would be expected to bear the patient's weight, the purpose of the sensor 100 generally being to provide some estimate of the patient's location in the bed. Generally speaking, and according to a first preferred embodiment, the mat 100/monitor 50 combination works as follows. As is illustrated in FIGS. 7 and 8, a typical pressure sensitive mat contains an inner non-conductive layer 710, which is "sandwiched" between two outer flexible non-conductive layers 730 and 740 which are conventionally made of some sort of thin plastic-like material. Cut into the central spacer 710 are one or more apertures 720 which are sized so as to allow the inner faces 735 and 745 of the outer members 730 and 740 to come into contact when weight is placed on the mat 700. It is conventional to treat the inner surfaces 735 and 745 with an electrical conductor of some sort (e.g., conductive-based ink, vacuum deposited metal or other conductive material, etc.) so that an attached patient monitor 50 can determine whether or not the two faces 735 and 745 have come into contact by means of a simple continuity check through electrical leads 330.

Figure 9A:
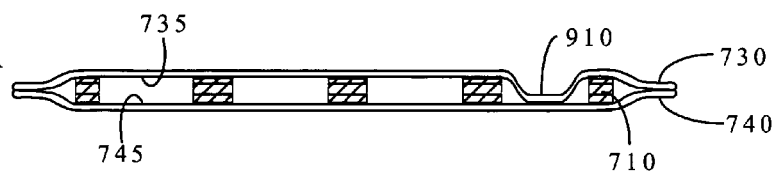
FIG. 9 contains a longitudinal cross section of the mat of FIG. 7 after weight has been applied to the mat at different locations.
Figure 9B:
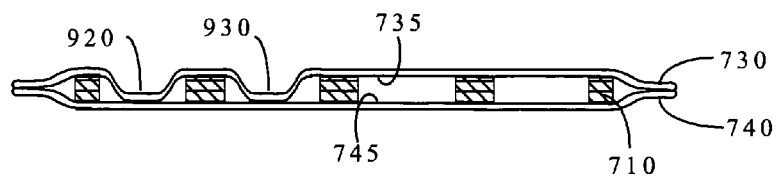

As is illustrated in FIGS. 9A and 9B, the inner faces 735 and 745 will come into contact at different locations, depending upon where pressure has been placed on the mat 700. For example, FIG. 9A represents a situation where the patient's weight rests near the right-most end of the mat 700 which produces a closure at contact point 910. On the other hand, FIG. 9B illustrates a case where a patient's weight is spread about near the left end of the mat 700, which results in contact points 920 and 930.

For purposes of the instant embodiment, it is desirable to measure at least the distance from, say, the left end of the mat (the end nearest the electrical line 750) to the nearest point where the patient compresses the mat into contact. Changes in the value of that measurement will reflect changes in the position of the patient on the mat 700 and in the bed.

The distance to the nearest contact point might be determined in many ways. In the event that the mat is a conventional pressure sensitive mat, the distance to the nearest contact point might be determined, for example, by measuring the resistance in the patient detection circuit, with lower resistances being associated with contact points nearer the entry point of the electrical line 750. As another example, a voltage pulse could be sent into the mat and the time until its return noted—contact points being more distant will result in longer transit times for the voltage pulse. "Longer" of course, would necessarily be measured in pico-seconds. As still another example, the capacitance of the patient circuit could be measured, with higher capacitances being associated with more contact area between the patient and the mat. As a further example, it is possible to induce an oscillation in the patient detection circuit, where the frequency of the induced oscillation is indicative of the patient position. Those skilled in the art will recognize that these sorts of methods, and many others, could be used to sense the patient's position on a conventional unmodified pressure sensitive mat.

Figures 10A, 10B, 10C:
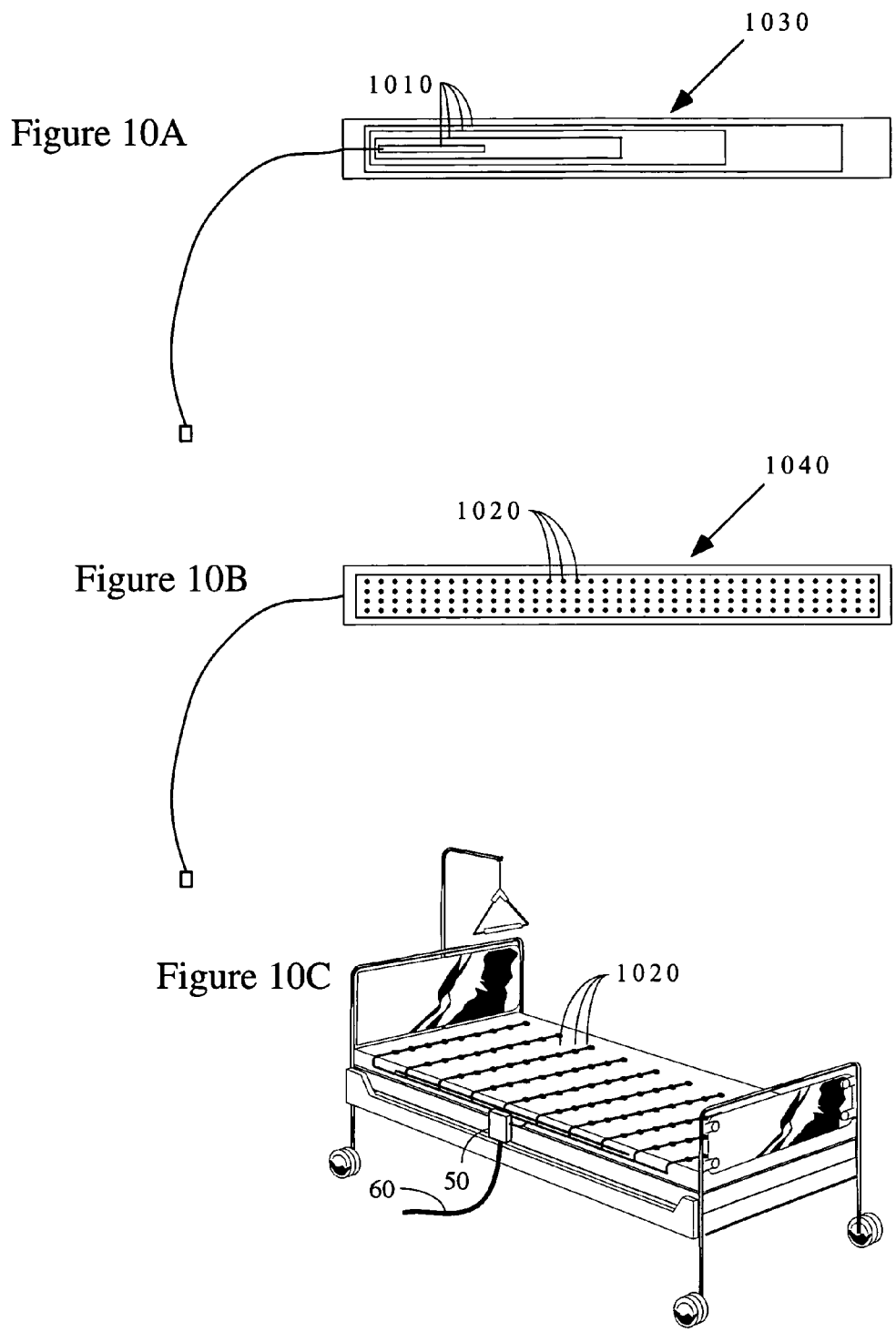
FIG. 10 illustrates some mat-type sensors that would be suitable for use with the instant invention.

According to another preferred embodiment, there are provided mat-type patient position sensors that are constructed especially for the purpose of determining the location of the patient thereon. A first preferred sensor embodiment may be found within the teachings of U.S. patent application Ser. No. 10/776,959, now U.S. Pat. No. 6,987,232, the disclosure of which is incorporated herein by reference. As is generally indicated in FIG. 10, there are many other ways that such a mat might be constructed. As a next examples in the embodiment of FIG. 10A a patterned conductive array 1010 has been applied to the inner surface of the non-conductive outer mat member 730 of a pressure sensitive mat 1030. By evaluating the continuity of the different pattern elements 1010 it is possible to determine location of the weight bearing portion of the patient nearest the left terminus of the mat.

As still another example, the embodiment of FIG. 10B illustrates that a grid of individual sensor points 1020 might be used to more precisely determine the location of the patient. By separately monitoring the status of each of the sensor points 1020, it will be possible to accurately determine the location of the patient who is positioned thereon. Note that these sensors might be part of a pressure sensitive mat 1040, in which case they could be electrically conductive "points" 1020 that would exhibit continuity when pressure from the patient's weight moved the illustrated mat-half into contact with another conductive surface. However, more generally these sensors could be temperature sensors (warmth at a temperature sensor being indicative of a patient location) or any other sort of sensor that would respond when the patient was proximate thereto. Further, in some preferred embodiments the individual sensor points could be made to be integral to the bed and/or its surface. Preferably, each of the sensor points 1020 would be separately identifiable by the CPU 310, so that the patient's position could be accurately determined at any point in time.

As still another example, the mat might be manufactured in the form of a sealed tube or pillow containing air or some other gas. As the patient moves and shifts his or her weight on the mat, pressure differences will be produced. Further, an overall increase in pressure will be correlated with the amount of occlusion of the mat by the patient. Thus, by monitoring the pressure of the gas within the mat, it is possible to determine when the patient changes position and, thus, whether or not he or she needs to be turned. Of course, those of ordinary skill in the art will recognize, as is indicated in FIG. 10C, that the collection of sensor points 1020 contained within the mat 1040 might be made to be any preferred size, including a size that is commensurate with the size of the mattress. As is indicated in FIG. 10C, the sensor points 1020 might be sized to cover the entire mattress and placed on top of it, within it, or below it according to the desires of the designer.

As another example, inductance-based position determination may also be used with a mat-type embodiment. As should be clear to those of ordinary skill in the art, the inductance exhibited by a mat will vary depending on the position of the patient on the mat and the contact area between the patient and the mat. Thus, by continuously measuring inductance it is possible to track patient motion in the bed, chair, etc. The precise method by which inductance changes are related to the patient's motion will depend on a number of mat parameters and may need to be determined empirically for each type of mat.

As a further example, the instant inventors contemplate that a grid of piezoelectric elements (e.g., solid-type or flexible-film-type) might be placed within a mat-type sensor in a regular (e.g., rectangular grid) pattern generally similar to that of FIG. 10A. Of course, it is well known that piezoelectric materials generate an electrical current when stressed, so it is possible to locate the patient on the mat by determining which of the various piezoelectric elements in the grid is currently experiencing stress in the form of weight/pressure from the patient. Needless to say, if the patient moves and thereby changes his or her weight distribution on the mat, the particular elements that are stressed will change, thereby giving an indication of the patient's new position.

Turning now to FIG. 12 wherein other preferred embodiments are presented, FIG. 12A indicates generally how an optical source 1215 can be used to determine a patient position. Preferably, the device 1210 will be oriented transverse to the direction the patient is laying and the patient thereafter placed thereon. The device 1210 might be, for example, a film, a sheet, or tubing of an internally-clear material such as plastic that is elastically deformable and which is at least partially reflective to light at its end 1255. In this embodiment—which is shown in FIG. 12A without a patient being present thereon—light energy 1215 is introduced into device 1210 at one end. Light 1245 then travels through the apparatus 1210, is reflected at its remote terminus 1255 and returns 1250 to the originating end where it emerges as measurable light energy 1220. FIGS. 12B and 12C indicate how the instant embodiment works when a patient is present and resting on the device 1210. In these figures, depression 1225 marks where the weight of a patient bends the device 1210. At least some of the light rays 1290—and in some cases substantially all of such light rays—that formerly traveled to the end of the device 1210 and were reflected 1295, now are intercepted and reflected by the curve 1225 induced by the patient's weight. The net result is that the returning light energy 1295 will be measurably changed because it has traveled a shorter distance through the attenuating medium of the apparatus 1210. Thus, the brightness of the emitted/reflected light energy 1260 is a measure of the distance that the light has traveled, which corresponds to the closest point at which the patient depresses the device 1210. Similarly, if sensitive enough measurements are made, it will be seen that the time for light to be reflected and return is shorter in the case of FIG. 12B than in the un-deformed embodiment of FIG. 12A. Thus, the time to travel through the embodiment 1210 and return to the point of origin is also a measure of the point of nearest compression. (By way of example only, this transit time might be measured via time domain reflectometry/timed differencing).

Similarly, the example of FIG. 12C would exhibit higher attenuation than the example of FIG. 12B and lower attenuation than the example of FIG. 12A. Thus, the amount of attenuation (or brightness of the emerging reflected light 1220, 1260, and 1265) can be used to provide estimates of the patient's current position. Finally, the same result holds with respect to transit times, with the transit time of the emerging light energy 1265 being longer than the example of FIG. 12B and shorter than the example of FIG. 12A.

In another preferred arrangement and as is illustrated in FIG. 12D, an array of longitudinal light sensors 1230 measures the amount of light received at each point along the length of device 1212. Obviously, if each of the sensors 1230 is monitored for received light energy, the far sensors will sense decreased light falling thereon at least as a function of the distance the light has traveled from its source. However, when a patient introduces a depression 1225 into the device, light reaching the sensors 1230 located on the other side of the depression 1225 will exhibit a more marked light drop than would have been present in the unoccupied case of FIG. 12A.

In still another preferred arrangement, FIG. 12E illustrates an embodiment wherein the thickness and resiliency of device 1214 is such that a patient at least partially compresses the upper surface toward the lower surface. One way to accomplish this is via the use of two different plastics of different compressibilities, although other arrangements are certainly possible. In the embodiment of FIG. 12E, light that might otherwise travel to the opposite end of the device 1214 is intercepted and reflected by the depression 1235 that is introduced by the weight of the patient. Thus, either the intensity of the reflected light 1270 or the received intensity at the longitudinal receptors 1230 can be used (as has been described above) to determine the location of the patient on the device.

Finally, in a last preferred arrangement and as is generally illustrated in FIG. 12F, there is provided another mat configuration wherein light is utilized to measure the patient's position and orientation on the sensor substantially as described above, but wherein point sources of light are placed in the interior of the mat instead of light sensors. In this embodiment the position and orientation of the patient is determined by the amount of light escaping from the edge(s) of the mat, which light is sourced within its interior. By way of explanation and turning to FIG. 12F, there is preferably provided a mat-type sensor 1216, which contains an internal light transmitting core 1240 which might be a light conductive plastic, an optical wave guide, etc. Within or proximate to the core 1240 are one or more light point sources 1242 which radiate light at a predetermined intensity level. Then, and according to a first preferred embodiment, a measure of the intensities of the light 1244 and 1246 that exits from each end of the core 1240 will be used to determine the patient location and the amount of the mat occluded by the patient. Those of ordinary skill in the art will recognize that when the mat 1216 is un-deformed a maximum intensity of light 1244 and 1246 will be measured by, say, a photoelectric cell positioned proximate thereto. However, when the mat 1216 has weight resting thereon, that will tend to limit the ability of light to travel from one edge of the mat to the other and the amount of transmitted light that is measured by one or more sensors 1230 situated near the edges of the mat 1216 will be correspondingly reduced. Thus, and by way of example only, by comparing the measured light intensity recorded by one or more of the in-mat sensors with known maximum possible intensities it is possible to estimate the proportion of the mat occluded and an approximate position.

In another preferred embodiment, the lights 1242 will be chosen to be different colors and some form of spectrographic analysis will be employed to determine how much of the mat is compressed and the patient's location. Those of ordinary skill in the art will recognize that if each of the light sources 1242 is chosen to be a different color it is readily possible to automatically determine which is "visible" from each end of the mat. Conventional spectrographic analysis, though expensive, would be one approach. In another more cost effective approach, a plurality of conventional photoelectric cells might be used, each of which would be made to be sensitive to a narrow band of light frequencies by, for example, covering each with a color filter or lens. In either case, the goal is to determine which frequencies are in present in the light 1244/1246 that is emitted from the mat 1216. Given a knowledge of the location and color of each lights in the mat, the nearest point of contact by the patient to each end of the mat can be readily determined.

Figure 2:
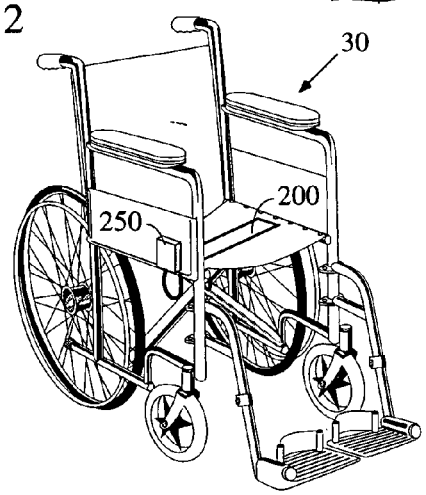
FIG. 2 illustrates a preferred embodiment of the instant invention for use in a wheel chair.

Note that any of the foregoing mat embodiments could also be placed on chairs, lounges, etc. As is generally illustrated in FIG. 2, mats that are suitable for use with beds 20 can, with some slight modifications well known to those skilled in the art, be adapted for use in wheelchairs 30 and/or stationary chairs in conjunction with chair monitor 250.

OTHER EMBODIMENTS

Figure 5:
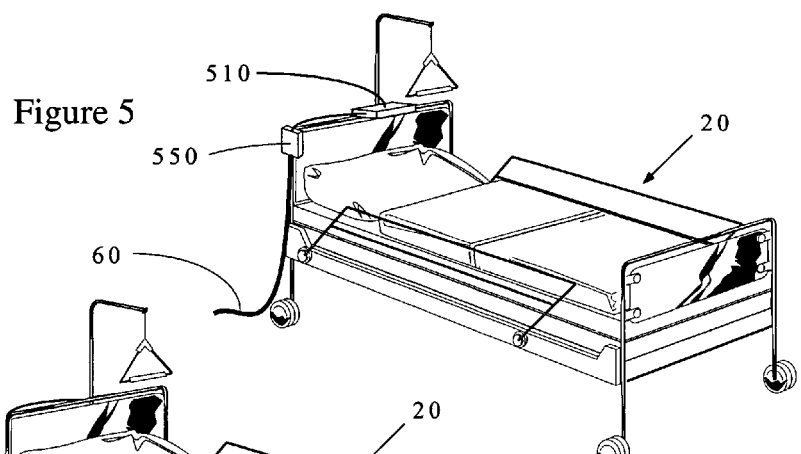
FIG. 5 contains an illustration of another preferred embodiment of the instant invention which utilizes a movement sensor to monitor the position of a patient in the bed.

FIG. 5 contains still another preferred embodiment of the instant invention. In this figure, a motion sensor 510 is positioned above the patient and continuously determines the current patient position and/or historical movement level. Note that the term "continuously" should, of course, be interpreted herein in its broadest sense to include periodic (i.e., regularly or irregularly time-spaced) re-measurement of the patient's position over some time period. However, in the preferred embodiment, a detector such as an infrared or ultrasonic motion detector will be used and will be continuously pulsed and monitored. This type of monitor 550 would be ideally suited to obtaining a general measure of the patient's movement level over time.

Figure 11:
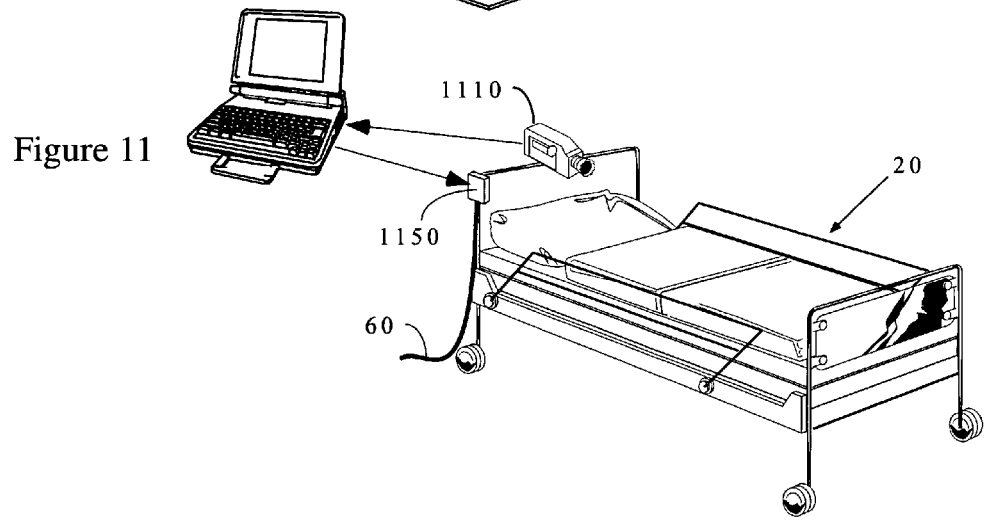
FIG. 11 illustrates another preferred embodiment, wherein the movement sensor is a video camera or similar photographic device.

Another variation of the previous embodiment involves the use of a conventional, infrared, etc., video camera 1110 or similar photographic device to record the position of the patient (FIG. 11). By converting the patient's image to digital values and using conventional image processing techniques, it is possible to track the position of a patient and determine when—and by how much—the patient has moved, if he or she moves. Of course, those sorts of mathematical operations might or might not require additional computational power beyond that which might be available within the monitor 1150. It is anticipated that a separate computer could be used to process the video information and transmit positional information back to the electronic monitor 1150, although other arrangements are certainly possible.

Figure 6:
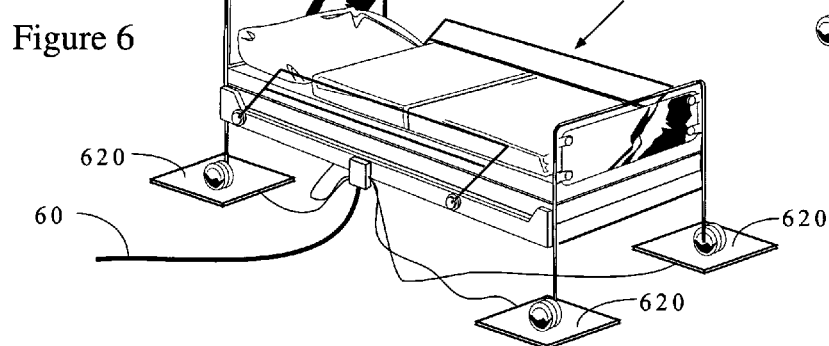
FIG. 6 contains an illustration of still another preferred embodiment of the instant invention which uses pressure sensitive pads positioned under the feet of the bed.

FIG. 6 contains a further preferred embodiment of the instant invention, wherein the weight that is bearing on each of the legs of a patient's bed is measured and, based on the weight distribution, a patient's location within the bed is determined. As a first preferred embodiment, each leg of the patient's bed has been placed on weight sensing pads 620. As is well known from elementary physics, the amount of weight that is measured on each bed leg will be dependent on the position of the patient in the bed. For example, if the patient has moved toward the left side of the bed, a weight measurement under the left legs will be higher than a weight measurement taken at the same time under the right bed legs. This simple fact can be used to at least roughly estimate the patient's location in the bed, as well as measure the overall time-based activity level of the patient. For example, by measuring the amount of weight change on each leg, it is possible to estimate the distance that the patient's center of gravity has moved. Obviously, this estimate could be used as has been discussed previously to screen for significant movement events, overall activity level, etc. Clearly, this same approach could be used with chair monitors, although it would in all likelihood be impractical for use on a wheel chair. Finally, it should be noted that the instant embodiment could be implemented, albeit somewhat inaccurately, with as few as a single weight sensor positioned under one of the bed legs, provided that certain parameters relating to the dimensions of the bed were known. In the event that a single sensor 620 is used, the CPU 310 would be preferably programmed to determine an initial pre-patient weight force on the single weight sensor 620. Then, after the patient is placed in the bed, the CPU 310 would determine the new weight bearing on the single leg under which the sensor 620 is located. Then, as the patient moves in the bed, that movement will be reflected in changes in the weight bearing on the single sensor 620. That weight change could then be converted at least approximately to movement in the bed.

Those of ordinary skill in the art will appreciate that the previous embodiment could be implemented in any number of ways, so long as the weight bearing on one or more legs can be determined. For example, instead of placing weight sensors 620 under each leg, the weight sensing apparatus could be made a part of and/or integrated into the bed leg or, alternately, the bed frame itself according to methods well known to those of ordinary skill in the art. In other embodiments, pneumatic bags/sensors or other pressure sensors might be placed under the mattress or frame and could similarly yield position information.

As another example of the sort of sensors that would be suitable for use with the instant invention, a further preferred embodiment involves attaching accelerometers to the bedsprings of patient's bed. Movement of the patient in the bed translates into vertical motion of the springs that support him or her, with springs that are relieved of weight expanding upward and those supporting additional weight compressing downward. By placing accelerometers (or other displacement indicators) that are sensitive to vertical movement at different points (e.g., attached to the bed springs), an estimate of the patient's position and historical activity level can readily be obtained.

Figure 13A:
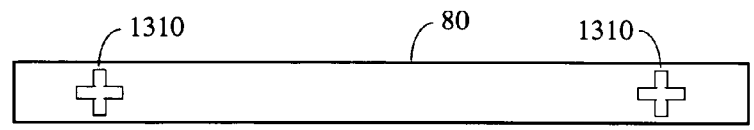
FIG. 13 illustrates another preferred embodiment, wherein strain gages or similar devices are affixed to a bed-frame and used to sense a patient's movement.

As still a further example of the sort of sensors that would be suitable for use with the instant invention, there is provided an arrangement wherein stain gages or similar devices to measuring the deformation of a structural member of a bed are utilized to determine at least an approximate location of the patient in the bed so that a determination can be made as to whether or not the patient has recently moved significantly. As is generally illustrated in FIG. 13A, one or more strain gages 1310 are preferably affixed to a structural member of the bed 80. According to the instant example, a horizontal bed mattress support member has been utilized although those of ordinary skill in the art will recognize that many other variations are certainly possible including, by way of example, positioning strain gages on the frame of a wheelchair 30 so as to monitor the weight distribution within the chair.

Strain gages 1310 are available in many different configurations and may be wired or wireless according to the application. As those of ordinary skill in the art will understand, stress/stain monitoring devices (e.g., piezoelectric devices, strain gages, etc.) convert motion or deformation of an object into an electronic signal. Typically, a change in capacitance, inductance, voltage, current, or resistance is utilized by the monitoring equipment to estimate the amount of strain experienced by the sensor. Standard equations then relate the observed changes in electrical property to the amount of deformation experienced by the monitored material.

The strain sensors 1310 are depicted in the form of a "cross" to indicate that it is preferable that at least two orthogonal components of the strain on the bed be measured. Although this is not strictly required, this arrangement will yield more accurate results than a simple one-dimensional measurement. Additionally, and as is typical with this technology, it is anticipated that the strain gages 1310 will be permanently affixed to one or more bed or chair members, preferably using an adhesive recommended by the bed or chair manufacturer.

Figure 13B:

Turning now to FIG. 13B, a schematic has been prepared which illustrates in a general way the underlying theory associated with the use of strain gages to measure patient movement. As can be seen in this exaggerated example, in an empty bed (FIG. 13A) the support members will be at least approximately horizontal. However, when a patient is placed in the bed or chair, the support members will tend to deform in a predictable way depending on the location of the patient. As can be seen in FIG. 13B, when the patient is located nearer the right hand side of the bed, the mattress support member 80 (which in this case is the member located at the foot of the bed) will exhibit more deformation near its right-hand side. Conversely, the left hand strain gage 1310 will experience less distortion. Further, it should be clear from this figure that the deformation angles in the support member 80 will yield at least approximately the location of the patient in the bed.

Note that the amount of deformation in the bed support member 80 as measured at the location of maximum deflection could be on the order of a few thousandths of an inch depending on the stiffness of the materials from which it is made. However, modern strain gages are easily capable of sensing such—and even smaller—deviations.

In the preferred embodiment, eight strain gages will be used: two located on each side of the bed frame in roughly the arrangement of FIG. 13, although many other arrangements would certainly be possible. Such an eight-sensor arrangement would yield some redundancy in the data collected and allow at least the center of gravity of the patient to be located with some reliability. That being said, many fewer strain gages could be used, perhaps as few as two 2-D gages. However, the instant inventors believe that the additional information obtainable from four or more sensors is worth the additional cost.

In practice, the instant embodiment would operate as follows. Either automatically, or upon initiation by a caregiver, the instant system will be recalibrated, preferably while the bed or chair is empty. As is well known to those of ordinary skill in the art, strain gages are susceptible to "creep" and, thus, preferred practice would be to periodically measure the amount of strain on the empty bed frame to establish a baseline value. Of course, the instant invention could automatically recalibrate if, for example, it senses that the bed is "empty" and has remained in that condition for some predetermined period of time.

During the time that a patient is present within the bed, the patient monitor will periodically re-determine the patient's position relative to the bed frame. As is generally indicated in FIG. 13B, at each re-determination information such as the inclination of the bed frame at each strain gage 1310 will be calculated. Note that in this variation, precision inclinometers could be used in place of the strain gages, provided that they are sufficiently accurate and that they are properly placed according to methods well known to those of ordinary skill in the art.

Given that sort of data for some number of sensors (preferably at least four), it is possible to locate within the bed frame at least the center of gravity of the patient's weight. After that point has been established, the invention will preferably continue to monitor the patient—and repeatedly recalculate the center of gravity—looking for a change in the location of that point. If a change in position is detected before the end of the patient turn interval, the instant invention will continue to further monitor the patient to see whether he or she returns to the original position within the persistence time period (i.e., before the previously compressed tissue has time to be sufficiently reoxygenated), e.g., ten minutes or some other interval selected by a caregiver. If, as has been explained previously, the patient returns to his/her original position prior to the expiration of this reoxygenation period, the instant monitor will determine that this was not a significant movement and, as a consequence, the monitor will preferably sound an alarm at the end of the initial patient turn interval if the patient does not move again. On the other hand, if the patient has moved significantly, the patient monitor will preferably reset the move timer and the nursing staff will either be notified that it is not necessary to turn the patient, or preferably not be signaled at all. Note that, for purposes of the instant disclosure, when the term "reoxygenate" is used, that term should be understood to mean reoxygenation to some minimally safe level. Although full reoxygenation of previously compressed tissues would always be desired in theory, practically speaking that goal is not easily attained, nor is it necessary. Those of ordinary skill in the art will recognize that the amount of time necessary to reoxygenate a patient's tissues will vary from patient-to-patient and depends on a number of factors. Thus, it is anticipated that in most cases the value of this time parameter will be left to the sound judgment of the physician/caregiver.

In another preferred embodiment, one or more inclinometers will be affixed to, for example, the patient's wrist, ankle, bicep, thigh, etc., or embedded in clothing such as vests, hats, foot wear, gowns, collars, etc. The purpose of such inclinometers is to make it possible for the patient's orientation in the bed to be monitored. As has been described previously, a central goal of such an arrangement is to monitor the patient for significant changes in position. Given even such basic information as the inclination of the patient's limbs or torso, those of ordinary skill in the art will recognize that it is possible to determine whether or not a patient has moved and whether or not that move is significant as that term is used herein.

Finally, in still another preferred arrangement, in the embodiment of FIG. 11, the patient's bed clothing will be outfitted with a plurality of optical targets to make it easier to automatically identify the patient's location and/or orientation via video camera 1110. If, for example, the patient were to be given a gown which had distinguishable optical targets imprinted thereon, for example, at the elbows, knees, back of the neck, etc., it would make the process of determining whether or not the patient has moved significantly more reliable. Those of ordinary skill in the art will understand that automatically identifying such targets within the video field is greatly simplified where the targets can be readily identified from the background.

CONCLUSIONS

It should be noted and remembered that the microprocessor 310 that is utilized as a component of the preferred monitor 50 has only one absolute requirement, namely that such a component must minimally be an active device, i.e., one that is programmable in some sense, that it is capable of recognizing signals from a bed mat or similar patient sensing device, and that it is capable of initiating the sounding of one or more alarm sounds in response thereto. Of course, these sorts of modest requirements may be satisfied by any number of programmable logic devices ("PLD") including, without limitation, gate arrays, FPGA's (i.e., field programmable gate arrays), CPLD's (i.e., complex PLD's), EPLD's (i.e., erasable PLD's), SPLD's (i.e., simple PLD's), PAL's (programmable array logic), FPLA's (i.e., field programmable logic array), FPLS (i.e., fuse programmable logic sequencers), GAL (i.e., generic array logic), PLA (i.e., programmable logic array), FPAA (i.e., field programmable analog array), PsoC (i.e., programmable system-on-chip), SoC (i.e., system-on-chip), CsoC (i.e., configurable system-on-chip), ASIC (i.e., application specific integrated chip), etc., as those acronyms and their associated devices are known and used in the art. Further, those of ordinary skill in the art will recognize that many of these sorts of devices contain microprocessors integral thereto. Additionally, given the modest requirements for the microprocessor of the instant invention, those of ordinary skill in the art will recognize that even discrete logic or analog chips could be assembled to perform the simple patient monitoring/alarm function discussed herein. Thus, for purposes of the instant disclosure the terms "processor," "microprocessor," "microcontroller", and "CPU" should all be interpreted to take the broadest possible meaning herein, and such meaning is intended to include any PLD or other programmable device of the general sort described above and elsewhere herein.

Those of ordinary skill in the art will recognize that it is also possible, although not preferred, to construct a monitor that performs the functionality described herein but which does not utilize a conventional microprocessor. That is, in another preferred arrangement a plurality of resettable timers will be utilized to determine whether or not the patient's movement has been significant. In this embodiment, separate timers will preferably be utilized for the patient turn interval and the persistence time period. Those of ordinary skill in the art will recognize that a sample hold circuit could be used to determine an initial location of the patient on the sensor. Thereafter, the patient's position could be regularly compared with the stored value until the patient moved, at which time the persistence timer would be started. If the patient returned to approximately the original position before the expiration of the persistence timer, the patient's movement would be deemed not significant. However, if the patient persisted in the new position longer than the persistence time, a significant move would be indicated and the patient turn interval timer would be reset. Additionally, a third resettable timer might be utilized if, for example, the patient location sensor were also utilized to monitor the patient for a bed-exit condition. In such a scenario, the third timer could be used to measure the delay time which is customarily utilized in patient exit monitors, the delay being measured between the time the patient leaves the mat and the start of the exit alarm. Those of ordinary skill in the art will recognize that such a delay helps prevent false alarms in those instances where a patient has merely shifted position within the bed or chair and momentarily removed his or her weight from the sensor.

Additionally, with respect to those embodiments taught herein that utilize a clock or timer or similar timing circuitry, those of ordinary skill in the art will understand that such functionality might be provided through the use of a separate dedicated clock circuit or implemented in software within the microprocessor. Thus, when "clock" or "time circuit" is used herein, it should be used in its broadest sense to include both software and hardware timer implementations.

Note further that a preferred electronic monitor of the instant invention utilizes a microprocessor with programming instructions stored therein for execution thereby, which programming instructions define the monitor's response to the one or more patient sensors in electronic communication therewith. Although ROM is the preferred apparatus for storing such instructions, static or dynamic RAM, flash RAM, EPROM, PROM, EEPROM, FRAM (i.e., ferromagnetic RAM), or any similar volatile or non-volatile computer memory could be used. Further, it is not absolutely essential that the software be permanently resident within the monitor, although that is certainly preferred. It is possible that the operating software could be stored, by way of example, on a floppy disk, a magnetic disk, a magnetic tape, a magneto-optical disk, an optical disk, a CD-ROM, flash RAM card, a ROM card, a DVD disk, or loaded into the monitor over a network as needed. Additionally, those of ordinary skill in the art will recognize that the memory might be either internal to the microprocessor, or external to it, or some combination. Thus, "program memory" as that term is used herein should be interpreted in its broadest sense to include the variations listed above, as well as other/similar variations well known to those of ordinary skill in the art.

It should also be noted that the term "nurse call" as that term has been used herein should be interpreted to mean, not only traditional wire-based nurse call units, but also any system for notifying a remote caregiver of the state of a patient, whether that system is wire-based (e.g., fiber optics, LAN) or wireless (e.g., R.F., ultrasonic, IR link, etc.). Additionally, it should be clear to those of ordinary skill in the art that it may or may not be a "nurse" that monitors a patient remotely and, as such, nurse should be broadly interpreted to include any sort of caregiver, including, for example, untrained family members and friends that might be signaled by such a system.

Finally, those of ordinary skill in the art should understand that the term "nurses' station" when used herein to describe to a preferred locale to which alarm sounds will be transmitted, should be interpreted in its broadest sense to include transmission of the alarm—either wireless, via a wired connection, or some combination—to nurses with pagers, wireless PDAs, cell phones, and AM/FM receivers (i.e., via lower power FM/AM radio), to name a few specific examples. In brief, is not necessary that there be a single fixed location for there to be a nurses' station as that term is used herein.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. An apparatus for reducing the risk of occurrence of pressure ulcers in a patient at rest on a support surface, comprising:
   (a) a patient location sensor for determining at least approximately a location of the patient on the support surface;
   (b) a time circuit;
   (c) a microprocessor in electronic communication with said patient location sensor and said time circuit, said microprocessor at least for
      (c1) determining an initial location of the patient,
      (c2) using said patient location sensor to determine that the patient has moved from said initial location,
      (c3) subsequently using said patient location sensor and said time circuit to determine whether or not said patient move from said initial location is a significant move,
      (c4) initiating a signal indicative of a state of the patient depending on whether or not said patient move from said initial location is a significant move; and,
   (d) an alarm in electronic communication with said microprocessor and responsive thereto, said alarm at least for responding to said signal indicative of a state of the patient to produce an alarm signal.

2. An apparatus for reducing the risk of occurrence of pressure ulcers in a patient according to claim 1, wherein said patient location sensor is selected from a group consisting of a bed mat and a chair mat.

3. An apparatus for reducing the risk of occurrence of pressure ulcers in a patient according to claim 1, wherein said patient location sensor is selected from a group consisting of a plurality of accelerometers, an infrared sensor, a video camera, an ultrasonic sensor, a plurality of strain gages, a plurality of inclinometers, a patterned conductive array, and a grid of individual sensor points.

4. An apparatus for reducing the risk of occurrence of pressure ulcers in a patient according to claim 1, wherein said alarm is selected from a group consisting of a speaker, a light, a buzzer, a pager, a piezoelectric device, a beeper, and, an audio annunciator.

5. An apparatus for reducing the risk of occurrence of pressure ulcers in a patient according to claim 1, wherein said apparatus is for use with a bed, said bed having at least four legs, and wherein said location sensor includes at least one weight sensor positioned proximate to at least one of said bed legs.

6. An apparatus for reducing the risk of occurrence of pressure ulcers in a patient according to claim 5, wherein said at least one weight sensor positioned proximate to at least one of said bed legs, comprises at least one weight sensor positioned beneath a lower terminus of at least one of said bed legs.

7. An apparatus for reducing the risk of occurrence of pressure ulcers in a patient according to claim 1, wherein
said patient location sensor is a mat containing a plurality of sensor points thereon,
each of said plurality of sensor points being separately identifiable by said microprocessor,
said sensor points being for use in determining at least approximately a location of the patient.

8. An apparatus for reducing the risk of occurrence of decubitus ulcers in a patient according to claim 7, wherein said sensor points are selected from a group consisting of temperature sensors, piezoelectric elements, resistive elements, inductive elements, conductive elements, and capacitive elements.

9. An apparatus for reducing the risk of occurrence of pressure ulcers in a patient according to claim 8, wherein said sensor points are integral to said support surface.

10. An apparatus for reducing the risk of occurrence of pressure ulcers in a patient according to claim 1, wherein
said patient location sensor comprises a plurality of sensor points,
each of said plurality of sensor points being separately identifiable by said microprocessor, and,
said sensor points being for use in determining at least approximately a location of the patient.

11. An electronic patient monitor according to claim 1, wherein said microprocessor is chosen from a group consisting of a microcontroller, a PLD, a CPLD, an EPLD, a SPLD, a PAL, an FPLA, an FPLS, a GAL, a PLA, an FPAA, a PSoC, a SoC, a CSoC, and an ASIC.

12. An apparatus for reducing the risk of occurrence of decubitus ulcers in a patient at rest on a support surface, comprising:
(a) a patient location sensor for determining at least approximately a location of the patient on the support surface;
(b) a time circuit;
(c) a microprocessor in electronic communication with said patient location sensor and said time circuit, said microprocessor at least for
  (c1) determining from said patient location sensor that the patient has moved,
  (c2) determining from said patient location sensor and said time circuit whether or not said patient move is a significant movement, wherein said significant movement is a patient movement to a new location that is maintained for a predetermined period of time,
  (c3) initiating a signal indicative of a state of the patient depending on whether or not said patient move is said significant movement;
(d) an alarm in electronic communication with said microprocessor and responsive thereto, said alarm at least for responding to said signal indicative of a state of the patient to produce an alarm signal.

13. An apparatus for reducing the risk of occurrence of decubitus ulcers in a patient according to claim 12, wherein said patient location sensor is selected from a group consisting of a bed mat and a chair mat.

14. An electronic patient monitor according to claim 12, wherein said microprocessor is chosen from a group consisting of a microcontroller, a PLD, a CPLD, an EPLD, a SPLD, a PAL, an FPLA, an FPLS, a GAL, a PLA, an FPAA, a PSoC, a SoC, a CSoC, and an ASIC.

15. An apparatus for reducing the risk of occurrence of decubitus ulcers in a patient according to claim 12, wherein said patient location sensor is selected from a group consisting of a plurality of accelerometers, an infrared sensor, a video camera, an ultrasonic sensor, a plurality of strain gages, and, a plurality of inclinometers.

16. An apparatus for reducing the risk of occurrence of decubitus ulcers in a patient according to claim 12, wherein said alarm is selected from a group consisting of a speaker, a light, a buzzer, a pager, a piezoelectric device, and a beeper.

17. An apparatus for reducing the risk of occurrence of decubitus ulcers in a patient at rest on a support surface, wherein is provided a predetermined patient turn interval, comprising:
(a) a patient location sensor for determining at least approximately a location of the patient on the support surface;
(b) a time circuit;
(c) a microprocessor in electronic communication with said patient location sensor and said time circuit, said microprocessor at least for
  (c1) determining from said patient location sensor that the patient has moved from a first position to a second position,
  (c2) determining from said patient location sensor and said time circuit whether or not said patient move to said second position is maintained for a period of time sufficient to reoxygenate patient tissues previously compressed when the patient was in said first position, thereby determining whether said move to said second position is a significant move,
  (c3) initiating a signal indicative of a state of the patient depending on whether or not said patient move is said significant movement;
(d) an alarm in electronic communication with said microprocessor and responsive thereto, said alarm at least for responding to said signal indicative of a state of the patient to produce an alarm signal.

18. An electronic patient monitor according to claim 17, wherein said microprocessor is chosen from a group consisting of a microcontroller, a PLD, a CPLD, an EPLD, a SPLD, a PAL, an FPLA, an FPLS, a GAL, a PLA, an FPAA, a PSoC, a SoC, a CSoC, and an ASIC.

19. An electronic patient monitor according to claim 17, wherein step (c3) comprises the steps of:
  (c3) initiating an alarm signal indicative of a state of the patient if during a period of time at least as long as said turn interval no significant move is detected, and, not initiating said alarm signal if during said period of time at least as long as said turn interval said significant move is detected.

20. A method of promoting tissue reoxygenation in a patient at rest on a support surface wherein is provided a patient turn interval, comprising the steps of:
(a) determining an initial location of the patient on the support surface;
(b) continuously monitoring the location of the patient for a period of time at least as long as said patient turn interval;

(c) if during said period of continuous monitoring the patient remains in said initial location for a period of time at least as long as said patient turn interval, generating an alarm signal at an end of said patient turn interval to notify a caregiver that the patient should be turned;

(d) if during said period of continuous monitoring the patient moves to a new location, but does not maintain said move to a new location for a period of time long enough to reoxygenate body tissues that were compressed when the patient was in said initial location, generating an alarm signal at an end of said patient turn interval to notify a caregiver that the patient should be turned; and, (e) if during said period of continuous monitoring the patient moves to a new location, and the patient maintains said move to a new location for a period of time long enough to reoxygenate body tissues that were compressed when the patient was in said initial location, signaling to the caregiver that the patient does not need to be turned.

21. A method according to claim 20, wherein said patient support surface is selected from a group consisting of a bed and a chair.

22. A method according to claim 20, wherein step (e) comprises the step of:

(e1) if during said period of continuous monitoring the patient moves to a new location, and the patient maintains said move to a new location for a period of time long enough to reoxygenate body tissues that were compressed when the patient was in said initial location, using a visual alarm to signal to the caregiver that the patient does not need to be turned.

* * * * *